United States Patent [19]

Thurman et al.

[11] Patent Number: 5,024,772
[45] Date of Patent: Jun. 18, 1991

[54] METHOD OF PRODUCING HPN AND MIXTURES THEREOF

[75] Inventors: Laurance R. Thurman, Clute; Joseph P. Dowd; Kathy J. Fischer, both of Lake Jackson, all of Tex.

[73] Assignee: BASF Corporation, Wyandotte, Mich.

[21] Appl. No.: 377,079

[22] Filed: Jul. 10, 1989

[51] Int. Cl.$^5$ .............................................. C07C 69/66
[52] U.S. Cl. ........................................ 252/1; 568/853; 568/854; 560/179; 560/189
[58] Field of Search ................ 568/853, 854; 528/272; 560/179, 189; 252/364, 142

[56] References Cited

U.S. PATENT DOCUMENTS

| | | | |
|---|---|---|---|
| 3,939,216 | 2/1976 | Wright | 568/854 |
| 4,021,496 | 5/1977 | Wright | 568/854 |
| 4,239,641 | 12/1980 | Perner et al. | 568/853 |
| 4,250,337 | 2/1981 | zur Hausen et al. | 568/853 |
| 4,665,219 | 5/1987 | Merger et al. | 560/189 |
| 4,851,592 | 7/1989 | Morris | 568/853 |

FOREIGN PATENT DOCUMENTS

| | | | |
|---|---|---|---|
| 66/14413 | of 1966 | Japan | 568/853 |
| 67/20521 | of 1967 | Japan | 568/853 |

Primary Examiner—John S. Maples
Assistant Examiner—Shean C. Wu
Attorney, Agent, or Firm—Cary W. Brooks; Karen M. Dellerman

[57] ABSTRACT

A process for producing 2,2-dimethyl-3-hydroxypropyl-2,2-dimethyl-3-hydroxypropionate (HPN) and neopentyl glycol (NP) blends from a neopentyl glycol production by-product stream containing neopentyl glycol, hydroxypivalic acid, and HPN using an acid catalyst.

19 Claims, 2 Drawing Sheets

METHOD OF PRODUCING HPN AND MIXTURES THEREOF

BACKGROUND OF THE INVENTION

1. Field of the Invention

The invention is directed to a method of producing 2,2-dimethyl-3-hydroxypropyl-2,2-dimethyl-3-hydroxypropionate (HPN). More particularly, the invention is directed to a method of producing HPN from the by-product stream of a neopentyl glycol (NP) production process.

2. Description of the Related Art

Various processes for the production of neopentyl glycol have associated with them the production of undesirable by-products which are often burned as wastestream. Heretofore, numerous attempts have been made to recover neopentyl glycol from by-product streams or to convert by-product stream components into desirable products.

Duke, Jr., et al, U.S. Pat. No. 3,340,312 discloses a process wherein mixtures of hydroxypivaldehyde and isobutyraldehyde can be hydrogenated in the presence of a copper-chromium oxide hydrogenation catalyst to yield isobutanol and neopentyl glycol.

Wright, U.S. Pat. No. 3,939,216 discloses a process for recovery of neopentyl glycol from a waste streams containing neopentyl glycol and water by contacting the by-product stream with isobutyraldehyde and subsequently separating this by-product stream into an organic stream containing neopentyl glycol and isobutyraldehyde and an aqueous stream essentially free of neopentyl glycol.

Holzrichter, U.S. Pat. No. 4,474,939, discloses eutectic mixtures of diols selected from the group consisting of neopentyl glycol, trimethylpentane diol, cyclohexanedimethanol, and 1,6-hexanediol.

Heretofore, there has been no process for the production of HPN and/or eutectic blends of neopentyl glycol and HPN from a by-product stream containing neopentyl glycol, hydroxypivalic acid (HPAD) and HPN.

SUMMARY OF THE INVENTION

It has now been discovered that HPN and eutectic blends of neopentyl glycol and HPN can be successfully produced from a neopentyl glycol production by-product stream containing neopentyl glycol, hydroxypivalic acid, and HPN. The neopentyl glycol production by-product stream is contacted with an acidic catalyst to cause the esterification of the neopentyl glycol and hydroxypivalic acid (HPAD) components of the by-product stream to produce HPN. Optionally, HPN may be added to the by-product stream to produce a eutectic blend of neopentyl glycol and HPN diol containing about 35 percent to about 100 percent HPN diol.

Objects, features and advantages of the instant invention are to provide: a novel method for making HPN and NP/HPN blends as well as a method of converting a neopentyl glycol production by-product stream to valuable products; a product which can comprise up to 100 percent HPN; a product blend of NP/HPN ranging from about 35 percent to about 100 percent by weight of HPN; a product blend which is a liquid at temperatures equal to or near room temperature. Other advantages are to provide: a product blend which can be shipped in a liquid state which is particularly economical and avoids the necessity of transportation equipment capable of maintaining high temperatures necessary for products containing a higher concentration of neopentyl glycol; a product blend which upon refinement does not require further heating to liquify the product which would otherwise be necessary if the product contained the higher concentration of neopentyl glycol. Further advantages are to provide: a product blend which is more conveniently and economically stored and transferred due to its liquid state; and a product blend which eliminates the costly and awkward task associated with dumping bags of solid material necessitated by blends having higher concentrations of neopentyl glycol.

BRIEF DESCRIPTION OF THE DRAWINGS

These and other objects, features and advantages of this invention will be apparent from the following detailed description, appended claims and drawings in which:

DESCRIPTION OF THE PREFERRED EMBODIMENTS

In accordance with the instant invention, HPN and eutectic blends of neopentyl glycol and HPN are produced by the esterification of hydroxypivalic acid (HPAD) with neopentyl glycol using an acidic catalyst. The esterification may be carried out as a batch or continuous process. The esterification reaction is as follows:

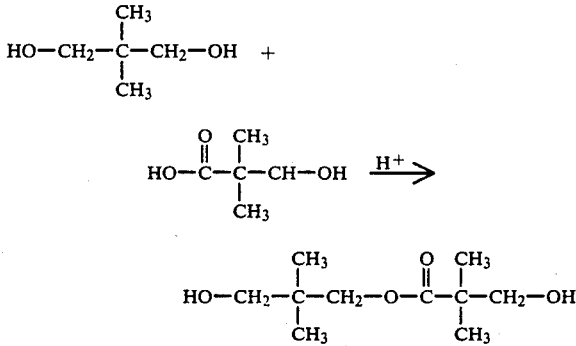

The production of HPN has associated with it a heavy doublet by-product which is a HPN ester. The concentration of these HPN esters in the final product is relatively low, as can be seen by the Examples which follow, and can be removed by further purification.

Figure 1:
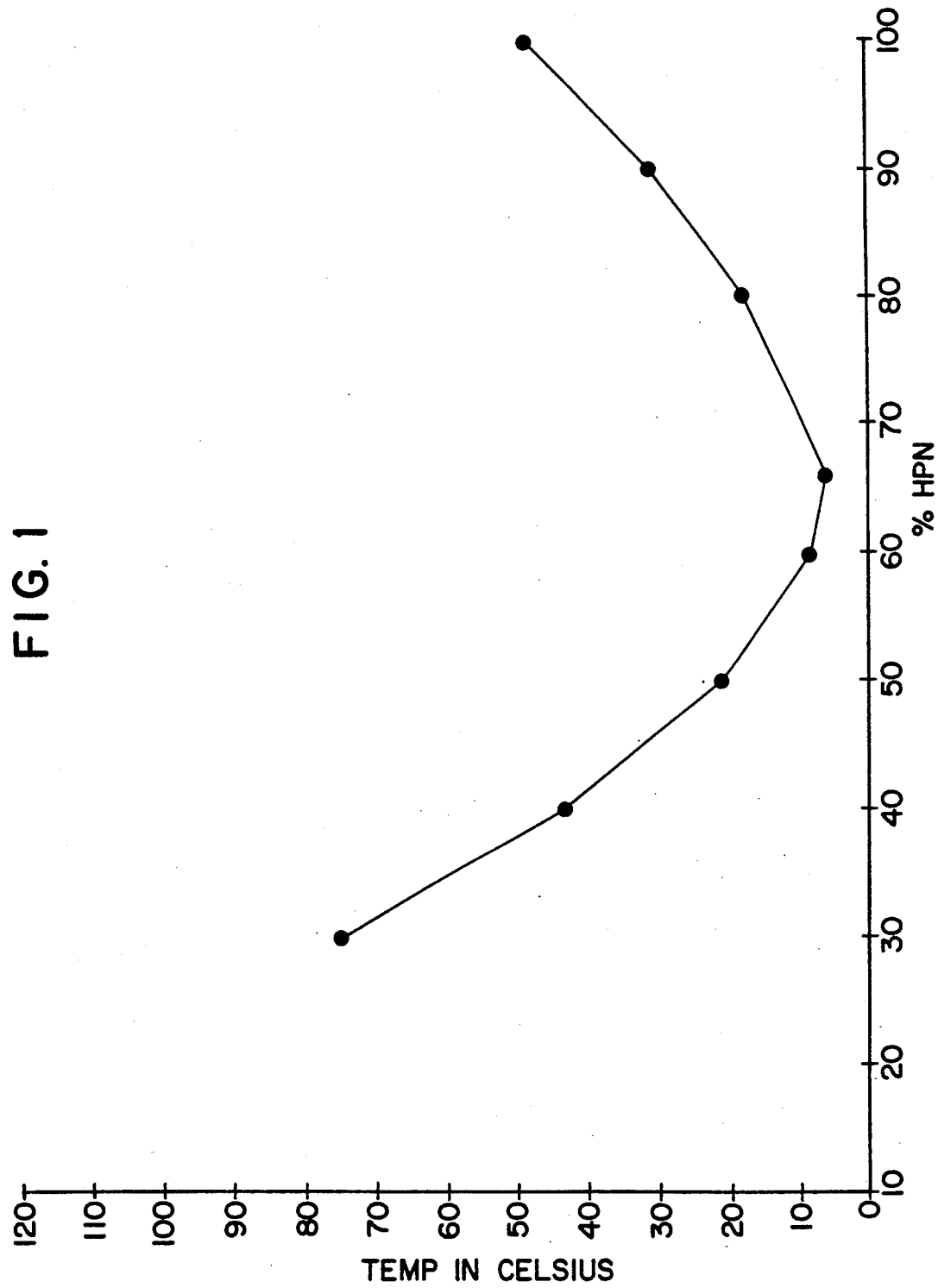
FIG. 1 is a graphic representation of the freezing points of NP/HPN eutectic mixtures identifying the eutectic composition.

It has been discovered that mixtures of neopentyl glycol and HPN form a eutectic material. Pure neopentyl glycol has a melting point range of 125°–130° C. and pure HPN has a melting point of 50° C. However, an eutectic blend of 40 percent of HPN and 60 percent of neopentyl glycol has a melting point of 40° C. FIG. 1 shows a range of melting points of the eutectic material with respect to change in HPN concentration. Various blends of NP/HPN were prepared and subjected to a range of temperatures to arrive at the eutectic points illustrated in FIG. 1. As can be seen in FIG. 1, NP/HPN blends containing from about 35 percent to about 100 percent HPN are liquids at room temperature (25°) or relatively near room temperature. Blends having at least 35 percent by weight concentration of HPN can be transported utilizing conventional equipment having means for relatively low heating capacity to maintain such blends in a liquid state. Blends containing less than 35 percent HPN require specialized heating equipment to maintain the blend in a liquid state or must be shipped as a solid in bags or other suitable packaging and are thus undesirable.

The bottom streams from a neopentyl glycol production finishing tower contains approximately 10 to 85 weight percent neopentyl glycol. Typically such bottoms contain approximately 65 percent neopentyl glycol, 13 percent hydroxypivalic acid, and 20 percent HPN. Heretofore, such by-product streams were burned in a neopentyl glycol process plant waste boiler.

It was discovered that the hydroxypivalic acid and the neopentyl glycol from a neopentyl glycol by-product stream could be esterified in the presence of an acidic catalyst to produce HPN. The esterification reaction is the mechanism as indicated above.

Preferably, the acidic catalyst is a mineral acid such as sulfuric acid, and most preferably, an acidic resin. A suitable acidic resin is available from Rohm and Haas Co., Philadelphia, under the name Amberlyst 15, 35 or 36. The use of an acidic resin eliminates the corrosion problems associated with mineral acids and the like.

When sulfuric acid is utilized as the acid catalyst, preferably its acid strength in weight percent to the total stream being esterified ranges from about 0.2 percent to about 0.5 percent, and most preferably, from about 0.4 percent to about 0.5 percent.

Preferably, the esterification is carried out in the presence of heat such that the temperature of the by-product stream to be treated ranges from about 90° C. to about 190° C., preferably about 120° C. to 170° C., and most preferably, about 120° C. to 140° C.

The neopentyl glycol production by-product stream remains in contact with the acid catalyst for a time sufficient to achieve the desired esterification and the desired concentration of HPN in the product stream. Preferably, the retention time for contacting the neopentyl glycol production by-product stream and the acid catalyst ranges from about 3 minutes to about 25 minutes, and more preferably 10 minutes to about 17 minutes. A desirable product in addition to containing about 35 percent to about 100 percent HPN, will contain less than 1 percent hydroxypivalic acid (HPAD). The retention time ranges above are equally applicable to batch reactions. The product from the esterification may be further refined by distillation to obtain predetermined concentrations of NP, HPN, and HPAD.

As previously indicated, the concentration of neopentyl glycol in the by-product stream from the neopentyl glycol production may range from approximately 10 percent to 85 percent. HPN may be added to the by-product stream to reduce the concentration of neopentyl glycol in the by-product stream which is to be esterified. The addition of HPN to the by-product stream allows the end product from the esterification to be controlled such that it contains at least 35 percent HPN or less than 65 percent neopentyl glycol and is thus a liquid at near room temperature. Furthermore, the addition of HPN to the by-product stream may be used to produce a product stream containing a predetermined concentration of HPN. To this end, HPN may be added to the by-product stream by recirculating the products stream and combining it with the by-product stream. Likewise, the acid strength concentration of the acidic catalyst, the reaction time, and the temperature at which the esterification occurs may be varied to produce a predetermined concentration of NP, HPN and HPAD in the product stream. The Examples which follow will more fully illustrate the flexibility of the instant invention process with respect to these variables.

Figure 2:
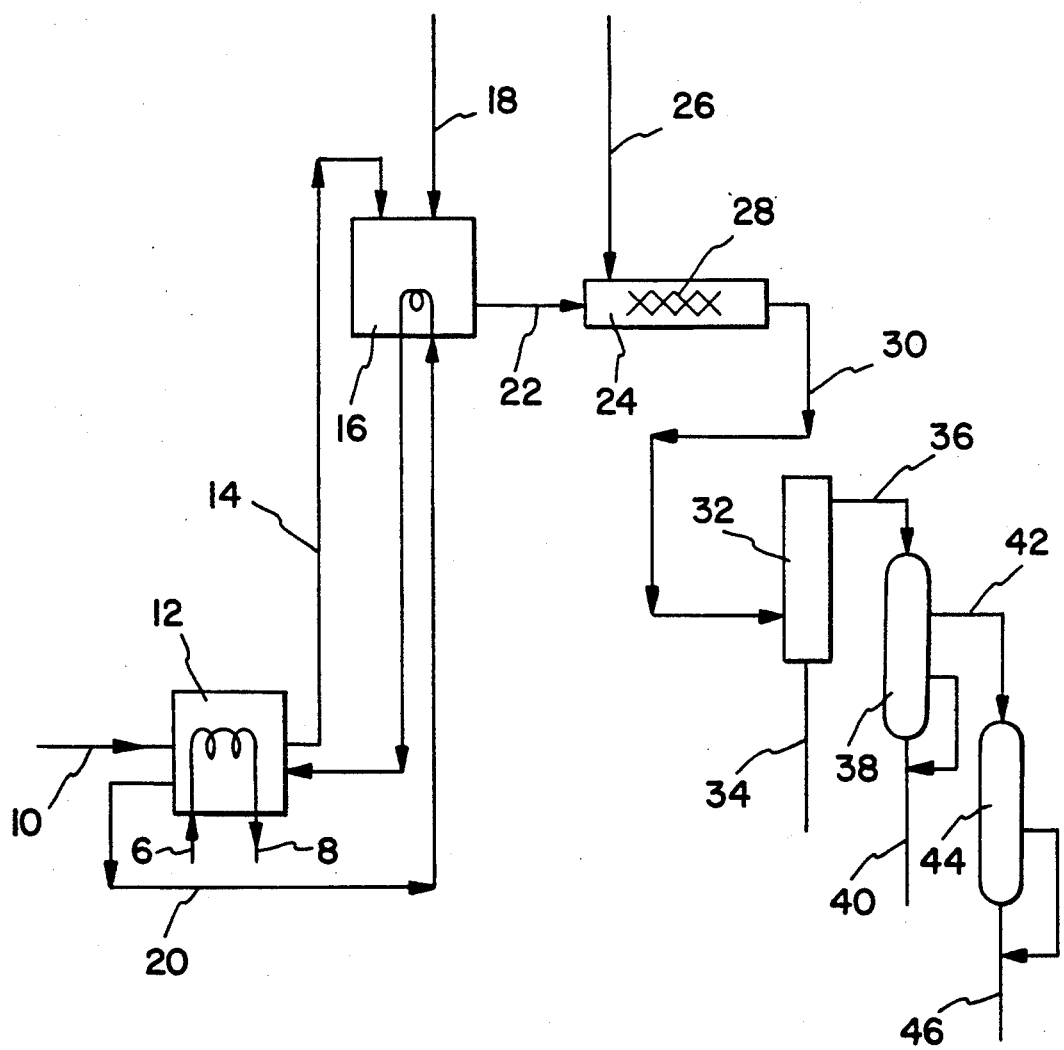
FIG. 2 is a schematic flow diagram of one embodiment of the subject invention process.

The following description of the process according to the instant invention has reference to FIG. 2, which is a schematic flow diagram of one embodiment of the overall process. A neopentyl glycol production by-product stream containing NP, HPAD, and HPN is continuously fed by line 10 directly from the neopentyl glycol production facility or from an intermediate source. The by-product stream is heated by a high temperature oil bath 12 to a predetermined temperature at which it is desired to conduct the esterification reaction. The heated by-product stream is fed by line 14 to a feed tank 16 to which a predetermined amount of HPN may be added by line 18 such that the product stream will have an associated predetermined concentration of HPN after the esterification process based on a preselected temperature, concentration of acid and reaction time. The material in the feed tank is heated by the high temperature oil bath by line 20 to achieve a desired temperature. From the feed tank, the material is continuously fed by line 22 to an acidic reaction zone 24. Within the acidic reaction zone 24, the reaction of neopentyl glycol and hydroxypivalic acid is acidically catalyzed by contacting the by-product stream with an acidic resin or a concentration of mineral acid by line 26 which is preferably sulfuric acid. If a mineral acid is utilized as the acidic catalyst, it is preferred that the acidic reaction zone include a means for mixing the acid and the by-product stream such as a static mixer 28. The acidic reaction zone also includes a means such as piping for adjustably defining the reaction zone and for achieving a desired retention or reaction time between the by-product stream and the acidic catalyst. Following the acidic reaction zone, the product may be refined by passing the product through a wiped film evaporator 32 and a series of condensers 38, 44 to achieve a finished product 40 having a desired concentration of NP, HPAD, and HPN. Bottoms 34 and lights 46 are removed from the wiped film evaporator 32 and condenser 44. The esterification product may be further separated by a distillation process or other purification means.

The Examples which follow illustrate the practice of the subject invention. These examples are by way of illustration only, and should not be interpreted as limiting the scope of the invention in any way.

EXAMPLE 1

In this example, a batch esterification was run wherein 40 grams of neopentyl glycol production bottoms (by-product) material was heated to the temperature indicated in Tables II, III, IV, V, and VI. The bottoms material had the following concentrations in percent by weight:

TABLE I

| | |
|---|---|
| NP | 61.5 |
| HPAD | 12.1 |
| HPN | 26.4 |

A preselected weight percent of concentrated sulfuric acid as indicated in Tables II–VI was added to the bottoms material. The solution was then kept at the test temperature as indicated for reaction times of 8, 10, 15, and 17 minutes. When the time period had elapsed, a portion of the material was withdrawn and mixed with 50 percent by weight of cold deionized water to stop the reaction and the product was analyzed. The acid strength is in weight percent of the by-product stream material. The results of the esterification are shown in Tables II, III, IV, V and VI.

TABLE II

Esterifications at 150° C.

| Reaction Time (in minutes) | | Acid Strength (in wt. %) | | | | | |
|---|---|---|---|---|---|---|---|
| | | 0.2% | 0.25% | 0.30% | 0.35% | 0.40% | 0.50% |
| 8 | NP | 57.76 | 53.29 | 50.80 | 52.27 | 51.91 | 52.05 |
| | HPAD | 2.77 | 0.59 | 0.55 | <0.05 | 0.39 | 0.35 |
| | Lights | 1.82 | 1.20 | 1.19 | 0.41 | 0.81 | 0.96 |
| | HPN | 34.41 | 40.62 | 42.82 | 44.73 | 41.35 | 40.96 |
| | H. Doublet | 2.56 | 3.88 | 5.50 | 5.10 | 4.84 | 5.20 |
| 10 | NP | 54.98 | 50.93 | 50.57 | 51.22 | 53.50 | 50.94 |
| | HPAD | 4.13 | 0.41 | 0.34 | <0.05 | <0.06 | 0.34 |
| | Lights | 1.71 | 1.20 | 0.82 | 0.89 | 0.69 | 0.95 |
| | HPN | 35.52 | 42.43 | 42.76 | 41.84 | 40.22 | 41.45 |
| | H. Doublet | 2.8 | 4.53 | 5.14 | 5.82 | 4.78 | 5.74 |
| 15 | NP | 55.06 | 51.04 | 50.52 | 53.54 | 52.17 | 50.33 |
| | HPAD | 3.23 | 0.27 | <0.05 | <0.05 | <0.05 | <0.04 |
| | Lights | 1.71 | 1.07 | 0.77 | 0.62 | 0.70 | 0.80 |
| | HPN | 36.1 | 41.94 | 42.30 | 39.61 | 41.60 | 41.96 |
| | H. Doublet | 2.9 | 5.04 | 5.85 | 5.75 | 5.53 | 6.65 |
| 17 | NP | 54.32 | 50.33 | 50.26 | 39.03 | 51.18 | 50.91 |
| | HPAD | 1.78 | 0.23 | <0.05 | <0.05 | 0.18 | <0.04 |
| | Lights | 1.97 | 1.18 | 0.92 | 0.86 | 0.88 | 0.82 |
| | HPN | 38.14 | 42.15 | 42.48 | 51.08 | 42.45 | 41.14 |
| | H. Doublet | 3.1 | 5.34 | 5.97 | 8.17 | 5.34 | 6.59 |

TABLE III

Esterifications at 160° C.

| Reaction Time (in minutes) | | Acid Strength (in wt. %) | | | | | |
|---|---|---|---|---|---|---|---|
| | | 0.2% | 0.25% | 0.30% | 0.35% | 0.40% | 0.50% |
| 8 | NP | 54.66 | 55.17 | 52.30 | 54.04 | 52.62 | 52.95 |
| | HPAD | 1.84 | 1.10 | 0.119 | 0.166 | 0.224 | 0.242 |
| | Lights | 1.43 | 1.44 | 1.35 | 1.44 | 1.64 | 1.53 |
| | HPN | 38.21 | 37.28 | 40.40 | 39.29 | 39.89 | 39.02 |
| | H. Doublet | 2.25 | 2.7 | 4.99 | 4.37 | 4.74 | 5.04 |
| 10 | NP | 55.71 | 55.72 | 54.57 | 56.12 | 52.38 | 52.05 |
| | HPAD | 0.637 | 0.382 | 0.217 | 0.116 | 0.127 | 0.266 |
| | Lights | 1.38 | 1.37 | 1.39 | 1.45 | 1.701 | 1.74 |
| | HPN | 38.54 | 38.21 | 38.37 | 37.28 | 39.72 | 38.95 |
| | H. Doublet | 3.2 | 3.7 | 4.7 | 4.30 | 4.901 | 5.5 |
| 15 | NP | 53.57 | 53.25 | 54.04 | 51.84 | 51.48 | 60.64 |
| | HPAD | 0.126 | 0.129 | 0.09 | 0.09 | <0.03 | — |
| | Lights | 1.42 | 1.33 | 1.44 | 1.45 | 1.39 | 1.81 |
| | HPN | 40.13 | 40.21 | 37.99 | 39.9 | 40.50 | 33.62 |
| | H. Doublet | 4.0 | 4.23 | 5.46 | 5.33 | 5.96 | 3.4 |
| 17 | NP | 51.67 | 52.68 | 54.75 | 54.52 | 52.85 | 51.93 |
| | HPAD | 0.113 | 0.097 | 0.028 | 0.134 | 0.123 | 0.08 |
| | Lights | 1.60 | 1.45 | 1.48 | 1.49 | 2.16 | 1.83 |
| | HPN | 41.04 | 40.28 | 37.67 | 37.84 | 38.06 | 39.26 |
| | H. Doublet | 4.6 | 4.6 | 5.4 | 5.0 | 5.93 | 6.3 |

TABLE IV

Esterifications at 170° C.

| Reaction Time (in minutes) | | Acid Strength (in wt. %) | | | | | |
|---|---|---|---|---|---|---|---|
| | | 0.2% | 0.25% | 0.30% | 0.35% | 0.40% | 0.50% |
| 8 | NP | 55.21 | 52.68 | 49.76 | 51.52 | 50.53 | 49.47 |
| | HPAD | 4.49 | 0.99 | 0.51 | 0.24 | 0.31 | 0.40 |
| | Lights | 1.23 | 0.84 | 0.88 | 0.98 | 0.83 | 1.02 |
| | HPN | 34.96 | 40.80 | 42.99 | 41.58 | 42.52 | 42.11 |
| | H. Doublet | 3.16 | 4.31 | 5.42 | 5.38 | 5.72 | 6.67 |
| 10 | NP | 52.05 | 52.36 | 50.24 | 50.57 | 49.21 | 51.35 |
| | HPAD | 4.60 | 0.53 | 0.30 | 0.20 | 0.32 | 0.29 |
| | Lights | 1.13 | 0.55 | 0.65 | 1.04 | 0.69 | 0.96 |
| | HPN | 37.58 | 41.81 | 43.23 | 41.97 | 43.45 | 40.78 |
| | H. Doublet | 3.73 | 4.59 | 5.33 | 5.93 | 6.21 | 6.39 |
| 15 | NP | 52.32 | 51.49 | 49.45 | 49.54 | 49.55 | 49.75 |
| | HPAD | 3.57 | <0.06 | <0.07 | <0.06 | <0.07 | 0.17 |
| | Lights | 1.14 | 0.65 | 1.20 | 0.91 | 0.82 | 1.38 |
| | HPN | 38.34 | 42.59 | 43.20 | 42.11 | 42.57 | 40.79 |
| | H. Doublet | 3.73 | 4.96 | 6.13 | 6.64 | 6.83 | 7.16 |
| 17 | NP | 52.03 | 51.58 | 51.94 | 51.29 | 49.46 | 48.73 |
| | HPAD | 3.05 | <0.05 | <0.04 | No Peak | <0.06 | 0.25 |
| | Lights | 1.12 | 0.66 | 0.79 | 0.90 | 0.92 | 1.54 |

TABLE IV-continued

| | Esterifications at 170° C. | | | | | |
|---|---|---|---|---|---|---|
| Reaction Time | | Acid Strength (in wt. %) | | | | |
| (in minutes) | 0.2% | 0.25% | 0.30% | 0.35% | 0.40% | 0.50% |
| HPN | 38.93 | 42.38 | 40.91 | 41.00 | 42.30 | 41.05 |
| H. Doublet | 3.83 | 5.028 | 5.98 | 6.30 | 6.99 | 7.44 |

TABLE V

| | | Esterification at 120° C. | | | |
|---|---|---|---|---|---|
| Reaction | | 0.40% | | 0.50% | |
| Time | | #1 | #2 | #1 | #2 |
| 10 min | NP | 57.53 | 60.38 | 60.5 | 59.49 |
| | HPAD | 3.17 | 1.55 | 0.67 | 0.40 |
| | Lights | 0.70 | 1.94 | 1.31 | 1.48 |
| | HPN | 35.76 | 34.13 | 35.08 | 36.27 |
| | H. Doublet | 2.79 | 2.02 | 2.45 | 2.78 |
| 15 min | NP | 57.97 | 60.71 | 59.49 | 58.75 |
| | HPAD | 1.95 | 0 | 0.40 | 0.51 |
| | Lights | 0.66 | 2.58 | 1.09 | 0.86 |
| | HPN | 36.65 | 34.78 | 36.27 | 37.01 |
| | H. Doublet | 2.79 | 1.95 | 2.78 | 4.38 |
| 17 min | NP | 56.92 | 60.5 | 59.14 | 59.3 |
| | HPAD | 1.59 | 0 | 0 | 0.26 |
| | Lights | 0.62 | 2.05 | 1.36 | 1.03 |
| | HPN | 37.96 | 34.13 | 37.36 | 36.23 |
| | H. Doublet | 2.93 | 2.34 | 2.15 | 3.51 |

TABLE VI

| | | Esterification at 130° C. | | | |
|---|---|---|---|---|---|
| Reaction | | 0.40% | | 0.50% | |
| time | | #1 | #2 | #1 | #2 |
| 10 min | NP | 59.96 | 57.0 | 56.85 | 57.16 |
| | HPAD | 0.54 | 1.07 | 0.78 | 1.18 |
| | Lights | 0.68 | 0.72 | 0.72 | 0.72 |
| | HPN | 35.78 | 38.15 | 37.94 | 37.54 |
| | H. Doublet | 3.29 | 3.08 | 3.60 | 3.42 |
| 15 min | NP | 59.14 | 56.96 | 56.43 | 55.54 |
| | HPAD | 0.19 | 0.40 | 0.49 | 0.75 |
| | Lights | 0.80 | 0.52 | 0.70 | 0.68 |
| | HPN | 36.34 | 38.53 | 38.18 | 39.37 |
| | H. Doublet | 3.50 | 3.77 | 4.23 | 3.69 |
| 17 min | NP | 56.88 | 58.04 | 56.13 | 55.96 |
| | HPAD | Trace | 0.35 | 0.36 | 0.71 |
| | Lights | 0.72 | 0.64 | 0.48 | 0.67 |
| | HPN | 38.85 | 37.6 | 38.48 | 38.44 |
| | H. Doublet | 3.56 | 3.38 | 4.56 | 4.07 |

Example 1 illustrates that the production of HPN and NP/HPN blends can be accomplished by reacting a mixture containing NP, HPAD and HPN in the presence of an acid having a concentration ranging from about 0.2% to about 0.5%, over a reaction time ranging from about 8 to about 17 minutes, at a temperature ranging from about 120° C. to about 170° C.

EXAMPLE 2

In this Example, neopentyl glycol production bottoms were collected for esterification in a continuous process and separation. The original composition of the material is indicated in the tables which follow. The process equipment in this example was arranged substantially similar to that illustrated in FIG. 2 and included an internal coil feed tank, piping to achieve a 15 to 30 minute reaction time to allow esterification of the NP and HPAD, a static mixer to provide sufficient mixing of concentrated sulfuric acid with the neopentyl glycol production by-product stream, a 0.06 m² wiper film evaporator for purification, and condensers to fractionate the product and lights. A high temperature circulating oil bath, heating tapes, and circulating chilled and hot water baths provided heating and cooling requirements. The operating conditions of this process equipment was varied as indicated in Tables VII-XI for eight different esterification runs. The lines and process equipment set forth in Tables VII and XI are substantially those illustrated in FIG. 2. In runs 1, 2 and 5, HPN was added to the original by-product stream to alter the concentration of NP and thus produced a synthetic blend. Run number 8 was a batch run which also involved adding HPN to alter the concentration of NP in the original by-product stream to produce a synthetic blend.

TABLE VII

| PARAMETER | RUN 1 | RUN 2 |
|---|---|---|
| | Operating Conditions | |
| Temperature, °C. | | |
| Line 36 | 180 | 174 |
| Line 42 | 60-112 | 76-102 |
| Line 8 | 192 | 184 |
| Line 30 | 149 | 154 |
| Line 22 | 150 | 156 |
| Line 6 | 195 | 189 |
| Line 10 | 90 | 90 |
| Pressure, mmHg: | 26 | 28 |
| Flows, mLs per min: | | |
| Feed | 15 | 13.5 |
| $H_2SO_4$ | 0.05-0.075 | 0.048-0.066 |
| percent: | | |
| $H_2SO_4$ | 0.43 | 0.39 |
| Reaction Time, minutes: | 12 | 13.3 |
| | Analytical Results | |
| Original: | | |
| Purity, Wt. % | | |
| NP | 69.65 | 66.43 |
| HPAD | 7.84 | 8.88 |
| HPN | 20.36 | 23.13 |
| HPN-Ester | 0.82 | 0.70 |
| Acidity, Wt. % | 14.92 | 13.99 |
| Synthetic Blend: | | |
| Purity, Wt % | | |
| NP | 56.94 | 65.42 |
| HPAD | 7.71 | 7.81 |
| HPN | 32.46 | 25.36 |
| HPN-Ester | 0.80 | 0.56 |
| Acidity, Wt. % | 12.92 | 13.2 |
| Product: | | |
| Purity, Wt. % | | |
| NP | 51.5 | 61.18 |
| HPAD | 0.65 | 0.32 |
| HPN | 42.54 | 36.59 |
| HPN-Ester | 3.75 | 0.68 |
| Acidity, Wt. % | 1.77 | 0.94 |

Acidity: Calculated as % hydroxypivalic acid. 2.0 gms Sample in 30 mL water with phenolphthalein as indicator and 0.5 N KOH as titrant.

TABLE VIII

| PARAMETER | RUN 3 | RUN 4 | RUN 5 |
|---|---|---|---|
| | Operating Conditions | | |
| Temperatures, °C. | | | |
| Line 36 | 178 | 190 | 190 |
| Line 42 | 34 | 41 | 57 |
| Line 8 | 196 | 201 | 200 |

TABLE VIII-continued

| PARAMETER | RUN 3 | RUN 4 | RUN 5 |
|---|---|---|---|
| Line 30 | 120 | 120 | 121 |
| Line 22 | 123 | 121 | 120 |
| Line 6 | 200 | 205 | 204 |
| Line 10 | 110 | 110 | 110 |
| Pressure, mmHg: | 41–46 | 51–57 | 48–58 |
| Flows, mLs per min: | | | |
| Feed | 13.5 | 9.0 | 8.0 |
| $H_2SO_4$ percent: | 0.045–0.056 | 0.031–0.042 | 0.029–0.044 |
| $H_2SO_4$ | 0.38 | 0.41 | 0.46 |
| Reaction Time, minutes | 13.3 | 20.0 | 22.5 |
| *Analytical Results* | | | |
| Original: Purity, Wt. % | | | |
| NP | 60.40 | 66.29 | 69.24 |
| HPAD | 9.10 | 9.25 | 9.02 |
| HPN | 28.17 | 23.28 | 20.82 |
| HPN-Ester | 1.16 | 0.57 | 0.32 |
| Acidity, Wt. % | 15.10 | 15.79 | — |
| Synthetic Blend: Purity, Wt. % | | | |
| NP | — | — | 65.36 |
| HPAD | — | — | 8.84 |
| HPN | — | — | 24.69 |
| HPN-Ester | — | — | 0.46 |
| Acidity, Wt. % | — | — | 14.40 |
| Product: Purity, Wt. % | | | |
| NP | 57.69 | 51.68 | 52.84 |
| HPAD | 1.49 | 1.65 | 1.29 |
| HPN | 39.69 | 42.89 | 43.32 |
| HPN-Ester | 0.43 | 2.56 | 1.48 |
| Acidity, Wt. % | 3.20 | 3.35 | 2.95 |

TABLE IX

| PARAETER | RUN 6 | RUN 7 | RUN 8 (BATCH) |
|---|---|---|---|
| Temperatures, °C. | | | |
| Line 36 | 189 | 190 | 184 |
| Line 42 | 48 | 57 | 65 |
| Line 8 | 205 | 206 | 195 |
| Line 30 | 128 | 130 | 130 |
| Line 22 | 129 | 132 | 129 |
| Line 6 | 206 | 209 | 198 |
| Line 10 | 110 | 110 | 110 |
| Pressure, mmHg: | 50–56 | 59–66 | 50–66 |
| Flows, mLs per min: | | | |
| Feed | 8.0 | 8.0 | 8.5 |
| $H_2SO_4$ percent: | 0.030–0.050 | 0.020–0.051 | — |
| $H_2SO_4$ | 0.49 | 0.50 | 0.50 |
| Reaction Time, minutes: | 22.5 | 22.5 | 21.2* |
| Original: Purity, Wt. % | | | |
| NP | 65.79 | 64.83 | 63.16 |
| HPAD | 9.13 | 8.53 | 9.38 |
| HPN | 23.01 | 24.77 | 24.70 |
| HPN-Ester | 0.83 | 0.91 | 0.88 |
| Acidity, Wt. % | 14.75 | 15.17 | — |
| Esterified Product: Purity, Wt. % | | | |
| NP | — | — | 48.95 |
| HPAD | — | — | 0.48 |
| HPN | — | — | 42.49 |
| HPN-Ester | — | — | 6.51 |
| Acidity, Wt. % | — | — | 1.18 |
| Product: Purity, Wt. % | | | |
| NP | 59.09 | 54.10 | 51.39 |
| HPAD | 0.64 | 0.78 | 0.42 |
| HPN | 38.11 | 42.88 | 44.72 |
| HPN-Ester | 1.08 | 1.27 | 2.27 |
| Acidity, Wt. % | 1.29 | 1.74 | 0.99 |

*Plus 20 minutes at 150° C.

Example 2 illustrates that the production of HPN and NP/HPN blends can be accomplished by a continuous or batch process from a by-product stream containing NP, HPN and HPAD. Further, Example 2 illustrates that HPN can be added to the original by-product stream to affect the concentration of HPN and NP in the product.

EXAMPLE 3

In this example, the esterification product was subjected to a separation process by distillation. However, other means of purification may be utilized to change the concentration of the esterification product.

The esterification product was advanced from a feed tank to a distillation tower where the product was distilled at about 200° C. The distillation product taken overhead was passed through an entrainment separator having demister pads. The overhead product was advanced to a first condenser operated at 135° C. to produce a bottoms product of NP and HPN. The bottoms from the first condensers was advanced to a second condenser operated at 55° C. where lower boilers are removed. Two lots of the esterification product were separated in two runs. The two different esterification product compositions were as follows:

| | Lot A | Lot B |
|---|---|---|
| NP | 50.6 | 46.2 |
| HPAD | 1.1 | 0.4 |
| HPN | 41.8 | 41.6 |
| Heavy Doublet | 2.5 | 8.8 |
| Water | 2.9 | 1 |

Lot A was separated by taking overhead splits as indicated in Table X and produced the product composition shown. Lot B was separated by taking overhead splits as indicated in Table XI and produced the product composition shown.

TABLE X

Lot A Separation

| | Overheads Split (wt %) | | |
|---|---|---|---|
| Product Composition | 80 | 85 | 90 |
| Color (Pt-Co) (50/50 in $H_2O$), Slightly Turbid | 5–10 | 5–10 | 10–15 |
| NP (wt %) | 59.68 | 55.81 | 53.72 |
| HPAD (wt %) | 1.63 | 1.54 | 1.49 |
| HPN (wt %) | 37.08 | 40.68 | 42.31 |
| Heavy Doublet (wt %) | 0.37 | 0.34 | 1.01 |
| Freeze Point, °C. | 47 | 41 | 35 |
| Water Content, wt % | 0.62 | 0.61 | 0.53 |

TABLE XI

Lot B Separation

| | Overheads Split (wt %) | | |
|---|---|---|---|
| Product Composition: | 80 | 85 | 90 |
| Color (Pt-Co) (50/50 in $H_2O$), Turbid | 15–20 | 25 | 30 |
| NP (wt %) | 56.08 | 51.94 | 52.08 |

TABLE XI-continued

| | Lot B Separation | | |
| --- | --- | --- | --- |
| | Overheads Split (wt %) | | |
| Product Composition: | 80 | 85 | 90 |
| HPAD (wt %) | 0.72 | 0.71 | 0.62 |
| HPN (wt %) | 39.10 | 40.99 | 40.89 |
| Heavy Doublet (wt %) | 0.59 | 2.44 | 2.38 |
| Freeze Point, °C. | 30 | 21 | 15 |
| Water Content, wt % | 1.31 | 0.82 | 1.05 |

As can be seen from Tables X and XI, the concentration of HPAD and the freezing point of the esterification product can be lowered by subjecting the material to separation after the esterification process. Further, the separation process may be used to lower the concentration of NP and increase the concentration of HPN.

The embodiments of the invention in which an exclusive privilege or property is claimed are defined as follows:

1. A process for making a product mixture having a preselected concentration of a 2,2-dimethyl-3-hydroxypropyl-2,2-dimethyl-3-hydroxypropionate component comprising the steps of:
    a) heating the reaction mixture having a hydroxypivalic acid component and a neopentyl glycol component to a preselected temperature ranging from about 120° C. to about 170° C., said neopentyl glycol component ranging from about 10 percent to about 85 percent by weight of said reaction mixture,
    b) contacting said reaction mixture with a mineral acid having a preselected concentration ranging from about 0.2 percent to about 0.5 percent by weight of said reaction mixture, and
    c) adding an amount of 2,2-dimethyl-3-hydroxypropyl-2,2-dimethyl-3-hydroxypropionate to said reaction mixture sufficient to produce said product mixture having said preselected concentration of said 2,2-dimethyl-3-hydroxypropyl-2,2-dimethyl-3-hydroxypropionate component.

2. A process as set forth in claim 1 wherein said contacting step is accomplished over a period ranging from about 7 minutes to about 25 minutes.

3. A process as set forth in claim 1 further comprising the step of selectively removing other components in said product mixture by distillation.

4. A process as set forth in claim 1 wherein said product mixture comprises at least 35 percent by weight 2,2-dimethyl-3-hydroxypropyl-2,2-dimethyl-3-hydroxypropionate.

5. A process as set forth in claim 1 wherein said product mixture is a liquid at a temperature ranging from about 10° C. to about 125° C.

6. A process as set forth in claim 1 further including the step of increasing the concentration of said 2,2-dimethyl-3-hydroxypropyl-2,2-dimethyl-3-hydroxypropionate component by distilling said product mixture.

7. A process as set forth in claim 1 wherein said product mixture further comprises a hydroxypivalic acid component.

8. A process as set forth in claim 1 wherein said product mixture further comprises a neopentyl glycol component of less than 65 percent by weight of said product mixture.

9. A process as set forth in claim 8 further including the step of decreasing the concentration of said neopentyl glycol component by distilling said product mixture.

10. A process as set forth in claim 1 further comprising the step of distilling said product mixture to reduce said hydroxypivalic acid component to less than one percent by weight of said product mixture.

11. A method of making a mixture of diols comprising:
    forming a eutectic mixture comprising neopentyl glycol and 2,2-dimethyl-3-hydroxypropyl-2, 2-dimethyl-3-hydroxypropionate in the presence of less than 5% hydroxypivalic acid, wherein said eutectic mixture is a liquid at temperature ranging from about 0° C. to about 50° C. and said neopentyl glycol comprising not more than 65 weight percent of said eutectic mixture.

12. A method as set forth in claim 11 wherein said neopentyl glycol and 2,2-dimethyl-3-hydroxy-propyl-2,2-dimethyl-3-hydroxypropionate are present in said eutectic mixture in a weight ratio of about 65:35 to about 0.1:99.9.

13. A method as set forth in claim 11 wherein said neopentyl glycol and 2,2 dimethyl-3-hydroxy-propyl-2,2-dimethyl-3-hydroxy propionate are present in said eutectic mixture, in a weight ratio of about 65:35 to about 15:85.

14. A process of continuously making 2,2-dimethyl-3-hydroxypropyl-2,2-dimethyl-3-hydroxypropionate comprising the steps of:
    advancing a neopentyl glycol by-product stream containing at least hydroxypivalic acid and neopentyl glycol through an esterification zone wherein the esterification reaction of said hydroxypivalic acid and said neopentyl glycol is acidically catalyzed.

15. A process as set forth in claim 14 further comprising the step of heating said stream to a temperature ranging from about 120° C. to about 170° C.

16. A process as set forth in claim 14 further comprising the step of selectively separating other esterification products from said 2,2-dimethyl-3-hydroxypropyl-2,2-dimethyl-3-hydroxypropionate.

17. A process as set forth in claim 14 wherein said esterification reaction is acidically catalyzed by contacting said stream with a mineral acid.

18. A process as set forth in claim 17 wherein said mineral acid is present in a concentration ranging from about 0.2 percent to about 0.5 percent by weight in said stream.

19. A process as set forth in claim 17 further comprising the step of mixing said stream with said acid in said esterification zone.

* * * * *